(12) United States Patent
Miyazaki

(10) Patent No.: US 11,104,858 B2
(45) Date of Patent: Aug. 31, 2021

(54) LUBRICATING BASE OIL, LUBRICATING OIL COMPOSITION CONTAINING LUBRICATING BASE OIL, AND METHOD FOR PRODUCING LUBRICATING OIL COMPOSITION

(71) Applicant: KAO CORPORATION, Tokyo (JP)

(72) Inventor: Tatsuya Miyazaki, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/465,509

(22) PCT Filed: Nov. 6, 2017

(86) PCT No.: PCT/JP2017/039960
§ 371 (c)(1),
(2) Date: May 30, 2019

(87) PCT Pub. No.: WO2018/116664
PCT Pub. Date: Jun. 28, 2018

(65) Prior Publication Data
US 2020/0063057 A1    Feb. 27, 2020

(30) Foreign Application Priority Data
Dec. 21, 2016  (JP) .............................. JP2016-247979

(51) Int. Cl.
| | | |
|---|---|---|
| *C07C 65/17* | (2006.01) | |
| *C10M 105/38* | (2006.01) | |
| *C07C 53/126* | (2006.01) | |
| *C07C 63/06* | (2006.01) | |
| *C10N 20/02* | (2006.01) | |

(52) U.S. Cl.
CPC ......... *C10M 105/38* (2013.01); *C07C 53/126* (2013.01); *C07C 63/06* (2013.01); *C10M 2207/2845* (2013.01); *C10N 2020/02* (2013.01)

(58) Field of Classification Search
CPC ........ C10M 105/38; C10M 2207/2845; C10M 105/40; C07C 53/126; C07C 63/06; C07C 67/08; C07C 69/78; C10N 2020/02
USPC ....................................................... 508/479
See application file for complete search history.

(56) References Cited

U.S. PATENT DOCUMENTS

| | | | |
|---|---|---|---|
| 5,057,247 A | 10/1991 | Schmid et al. | |
| 5,503,761 A | 4/1996 | Ashcraft, Jr. et al. | |
| 2003/0153471 A1* | 8/2003 | Godici | C10M 105/38 |
| | | | 508/479 |
| 2003/0228986 A1 | 12/2003 | Bessonette et al. | |
| 2010/0181523 A1 | 7/2010 | Kelley et al. | |
| 2014/0045733 A1 | 2/2014 | Nogami et al. | |

FOREIGN PATENT DOCUMENTS

| | | |
|---|---|---|
| CN | 102876435 A | 1/2013 |
| CN | 103476911 A | 12/2013 |
| GB | 1 280 247 A | 7/1972 |
| GB | 2 060 624 A | 5/1981 |
| JP | 47-21090 Y | 7/1972 |
| JP | 49-43542 B1 | 11/1974 |
| JP | 51-84100 A | 7/1976 |
| JP | 56-115743 A | 9/1981 |
| JP | 61-287987 A | 12/1986 |
| JP | 63-170337 A | 7/1988 |
| JP | 8-60169 A | 3/1996 |
| JP | 2003-193087 A | 7/2003 |
| JP | 2003-268395 A | 9/2003 |
| JP | 2012-515251 A | 7/2012 |

OTHER PUBLICATIONS

International Search Report for PCT/JP2017/039960 dated Dec. 5, 2017.
Extended European Search Report, dated May 14, 2020, for European Application No. 17883555.9.
International Preliminary Report on Patentability and Written Opinion of the International Searching Authority for International Application No. PCT/JP2017/039960, dated Jul. 4, 2019, with English translation.
English translation of Chinese Search Report issued in the corresponding Chinese Patent Application No. 201780078038.2 dated May 7, 2021.

* cited by examiner

*Primary Examiner* — Prem C Singh
*Assistant Examiner* — Francis C Campanell
(74) *Attorney, Agent, or Firm* — Birch, Stewart, Kolasch & Birch, LLP

(57) ABSTRACT

Provided is a method of lubricating a sliding part by applying a lubricating base oil containing an ester compound to the sliding part. The ester compound contains a mixture of one or more compounds represented by a general formula (1) wherein $R^1$ and $R^2$ independently represent a hydrogen, a methyl, a benzoyloxy, a naphthoyloxy, or general formula (2) (—O—C(=O)—$R^5$), $R^3$ and $R^4$ independently represent a benzoyloxy group, a naphthoyloxy group, or general formula (2), and $R^5$ represents a linear C5-21 alkyl group, a branched chain C9-21 alkyl group, or a C5-21 cycloalkyl group that may also be substituted with an alkyl chain. The mixture contains a compound in which at least one among $R^1$ to $R^4$ is general formula (2), and the proportion, in the mixture, of a compound in which at least one among $R^1$ to $R^4$ is a benzoyloxy group or a naphthoyloxy group is 5-100 mole %.

20 Claims, No Drawings

LUBRICATING BASE OIL, LUBRICATING OIL COMPOSITION CONTAINING LUBRICATING BASE OIL, AND METHOD FOR PRODUCING LUBRICATING OIL COMPOSITION

TECHNICAL FIELD

The present invention relates to a lubricant base oil, a lubricant oil composition containing this lubricant base oil, and a method for producing the composition. The invention also relates to the use of the lubricant oil composition, and a lubricating method using the lubricant oil composition.

BACKGROUND ART

Lubricant oil is used in various fields in which friction decrease is required. In old times, natural fat and oil, petroleum purified products, and others were used. In recent years, however, synthetized lubricant oils have come to be synthesized and used in accordance with articles to be used. In particular, synthesized esters are excellent in thermal stability. Specific examples thereof include organic acid esters, phosphoric acid esters, and silicic acid esters.

Out of the organic acid esters, polyol esters (condensed esters each made from a polyhydric alcohol and a carboxylic acid) are used since the esters 1) are low in pour point and high in viscosity index to be wide in a use-temperature range thereof, 2) are high in flash point and small in evaporation quantity, 3) are excellent in thermal and anti-oxidization stabilities, 4) are good in lubricity, 5) have cleaning and dispersing effects, and 6) have biodegradability. In many fields, in particular, hindered esters are used since the esters are in thermal and anti-oxidization stabilities.

However, in recent years, with developments of industrial techniques, high productivity and operation stability have been constantly required; thus, lubricant oils have come to be required to be higher in endurance and higher in heat resistance.

Although synthesized esters are excellent in performance for lubricant oils, it is mentioned that the esters have a drawback that in the presence of water, their ester bonds are cut, i.e., the so-called hydrolysis thereof is caused. Thus, a synthesized ester has been desired which is high in hydrolysis resistance so that the ester can resist against being used in an environment in which the ester is exposed to water.

For example, Patent Document 1 discloses a high-temperature stable lubricant which is economical, is resistant against thermal decomposition, and is smaller in viscosity increment than the existing lubricants. This lubricant is suitable, particularly, for gas turbine engines derived from aircrafts. This lubricant includes a mixed polyol ester in which a carboxylic acid part of this ester includes (a) 2 to 40% by mole of an aromatic carboxylic acid and (b) 60 to 98% by mole of a C5 to C20 aliphatic carboxylic acid, and an alcohol part of the ester includes an aliphatic polyol.

Patent Document 2 discloses a synthesized ester base stock including a reaction product made from pentaerythritol for industries, and a carboxylic acid mixture. The carboxylic acid mixture includes (1) at least one C8-C10 carboxylic acid having 6 or less reactive hydrogen atoms, (2) at least one C5-C7 carboxylic acid having 6 or less reactive hydrogen atoms, and (3) at least one C6-C10 carboxylic acid having 6 or more reactive hydrogen atoms. This synthesized ester base stock is useful for producing turbo oil for aircrafts, and has an effect of restraining the production of deposits in a turbine engine for aircrafts.

Patent Document 3 discloses a synthesized polyol ester which consists substantially of a neutral esterified product made from a specified polyol compound selected as a hydroxyl component, and a specified mono-carboxylic acid and/or a poly-carboxylic acid as one or more acid components, and which is used to produce a temperature-stable lubricant oil dispersant and/or a lubricant grease.

Patent Document 4 discloses a complex ester which is suitable as a lubricant oil for gas turbines, in particular, for turbojet aircraft engines and stationary engines, and has a good stability, a low pour point and a high viscosity index, and which is produced by a reaction between a neopentylpolyol type polyol, an aromatic polycarboxylic acid, and an aliphatic monocarboxylic acid.

PRIOR ART DOCUMENTS

Patent Documents

Patent Document 1: JP-A-2003-193087
Patent Document 2: JP-A-8-60169
Patent Document 3: JP-A-63-170337
Patent Document 4 JP-B-47-21090

SUMMARY OF THE INVENTION

Problems to be Solved by the Invention

As described above, in the prior art, as lubricant oils, various ester compounds have been used. However, in order to improve productivity and operation stability, lubricant oils have been required which are higher in heat resistance, lubricity, and hydrolysis resistance. In particular, the ester in Patent Document 1 aims mainly to be used as a lubricant oil for gas turbine engines. A carboxylic acid in which the number of carbon atoms is small is suitable therefor. Consequently, the ester has a problem of being high in affinity with water, and low in oil-water separatability to be easily hydrolyzed.

Thus, an object of the present invention is to provide a lubricant base oil including an ester compound excellent in heat resistance, lubricity and hydrolysis resistance; a lubricant oil composition including the lubricant base oil; and a method for producing this composition.

Means for Solving the Problems

Accordingly, the present invention relates to a lubricant base oil including an ester compound, wherein: the ester compound includes a mixture including one or more compounds (each) represented by the following general formula (1):

[Formula 1]

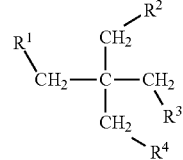

(1)

wherein $R^1$ and $R^2$ each independently represent a hydrogen atom, a methyl group, a benzoyloxy group, a naphthoyloxy group or a general formula (2): $-O-C(=O)-R^5$, and $R^3$ and $R^4$ each independently represent a benzoyloxy group, a naphthoyloxy group or the general formula (2): —O—C(=O)—$R^5$ wherein $R^5$ represents a linear alkyl group having 5 to 21 (both inclusive) carbon atoms, a branched alkyl group having 9 to 21 (both inclusive) carbon atoms, or a cycloalkyl group having 5 to 21 (both inclusive) carbon atoms and optionally substituted with an alkyl chain; the mixture includes a compound about which at least one of the groups $R^1$ to $R^4$ is the general formula (2): —O—C(=O)—$R^5$; and a proportion of a compound about which at least one of the groups $R^1$ to $R^4$ is the benzoyloxy group or the naphthoyloxy group in the mixture is from 5 to 100% by mole both inclusive.

The present invention also relates to a lubricant oil composition, including the above-defined lubricant base oil.

Furthermore, the present invention relates to a method for producing the above-defined lubricant base oil, including the step of producing a mixture including one or more compounds (each) yielded by condensing one or more alcohols and one or more carboxylic acids and (each) represented by the general formula (1), wherein: the alcohol(s) include(s) a polyhydric alcohol represented by the following general formula (3):

[Formula 2]

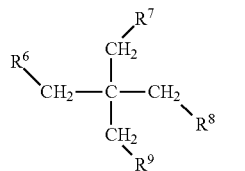

(3)

wherein $R^6$ to $R^9$ each independently represent a hydrogen atom, a methyl group or a hydroxyl group, and further at least two of $R^6$ to $R^9$ each represent the hydroxyl group; the carboxylic acid(s) include(s) one or more aromatic carboxylic acids and one or more aliphatic acids; the aromatic carboxylic acid(s) includes(s) benzoic acid and/or naphthoic acid; and the aliphatic carboxylic acid(s) include(s) at least one monocarboxylic acid selected from linear alkyl aliphatic acids each having 6 to (both inclusive) carbon atoms, branched alkyl aliphatic acids each having 10 to 22 (both inclusive) carbon atoms, and cycloalkanecarboxylic acids each having 6 to 22 (both inclusive) carbon atoms and each optionally substituted with an alkyl chain.

Effect of the Invention

Details of the action mechanism of advantageous effects of the lubricant base oil according to the present invention are partially unclear; however, the mechanism is presumed as described below. However, the invention may not be interpreted with limitation to this action mechanism.

The present invention is a lubricant base oil including a mixture including one or more ester compounds (each) represented by the general formula (1). About the ester compound having an ester chain derived from a benzoyloxy or naphthoyloxy group, the ester chain is high in heat resistance, so that the ester compound is not thermally deteriorated even at high temperature to be stably present. Thus, it is presumed that the ester compound remains in the lubricant base oil or the lubricant oil composition without being polymerized or volatilized.

It is also presumed that in the ester compound, which has an ester chain derived from a benzoyloxy or naphthoyloxy group, molecules thereof are rarely entangled with each other by the rigidity of the structure thereof not to lower the lubricant base oil in lubricity, so that the lubricant base oil is also excellent in lubricity.

Furthermore, about the ester compound derived from any one of the linear alkyl groups having 5 to 21 (both inclusive) carbon atoms, the branched alkyl groups having 9 to 21 (both inclusive) carbon atom, and the cycloalkyl groups having 5 to 21 (both inclusive) carbon atoms and optionally substituted with an alkyl chain, the ester chain of this compound is high in hydrophobicity, so that the ester compound is not easily mixed with water. Thus, it is presumed that the hydrolysis of the ester bond of the ester compound is restrained so that the ester compound is improved in hydrolysis resistance.

In the mixture, the proportion of the compound about which at least one of $R^1$ to $R^4$ is a benzoyloxy or naphthoyloxy group is from 5 to 100% by mole both inclusive. It is also presumed that according to this matter, the above-mentioned mechanism acts sufficiently to produce a lubricant base oil high in heat resistance, lubricity and hydrolysis resistance.

MODE FOR CARRYING OUT THE INVENTION

The lubricant base oil of the present invention includes an ester compound, and the ester compound includes a mixture including one or more compounds (each) represented by the following general formula (1):

[Formula 3]

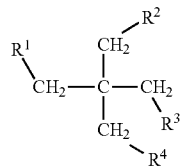

(1)

wherein $R^1$ and $R^2$ each independently represent a hydrogen atom, a methyl group, a benzoyloxy group, a naphthoyloxy group or a general formula (2): —O—C(=O)—$R^5$, and $R^3$ and $R^4$ each independently represent a benzoyloxy group, a naphthoyloxy group or the general formula (2): —O—C(=O)—$R^5$ wherein $R^5$ represents a linear alkyl group having 5 to 21 (both inclusive) carbon atoms, a branched alkyl group having 9 to 21 (both inclusive) carbon atoms, or a cycloalkyl group having 5 to 21 (both inclusive) carbon atoms and optionally substituted with an alkyl chain. The mixture is a mixture including plural compounds each represented by the general formula (1). However, a single compound represented by the general formula (1) is also usable. The lubricant base oil of the present invention denotes compounds which are main components of a lubricant oil composition, and are blended, together with various lubricant oil additives for giving various functions to the lubricant oil composition, into the composition to control the viscosity and other physical properties of the lubricant oil composition.

In order to improve each of the ester compounds in heat resistance and heighten the compound in kinetic viscosity, about $R^1$ to $R^4$, one or more of $R^1$ to $R^4$ are (each) a benzoyloxy or naphthoyloxy group. Two or more thereof are each preferably, three or more thereof are each more preferably, and four thereof are each even more preferably the benzoyloxy or naphthoyloxy group. In the meantime, about $R^1$ to $R^4$, in order to lower the ester compound in kinetic viscosity, three or less of $R^1$ to $R^4$ are each preferably, two or less thereof are each more preferably, and one thereof is even more preferably the benzoyloxy or naphthoyloxy group. In order to improve the ester compound in heat resistance and lower the compound in kinetic viscosity, the benzoyloxy group is preferred. In order to heighten the ester compound in kinetic viscosity, the naphthoyloxy group is preferred.

$R^5$ is a linear alkyl group having 5 to 21 (both inclusive) carbon atoms, a branched alkyl group having 9 to (both inclusive) carbon atoms, or a cycloalkyl group having 5 to 21 (both inclusive) carbon atoms and optionally substituted with an alkyl chain.

When $R^5$ is the linear alkyl group having 5 to 21 (both inclusive) carbon atoms, the number of the carbon atoms therein is preferably 6 or more, more preferably 7 or more, even more preferably 8 or more to improve the ester compound in heat resistance and hydrolysis resistance and heighten the compound in kinetic viscosity. In order to lower the kinetic viscosity, the number is preferably 17 or less, more preferably 11 or less, even more preferably 9 or less.

When $R^5$ is the branched alkyl group having 9 to 21 (both inclusive) carbon atoms, the number of the carbon atoms therein is preferably 11 or more, more preferably 13 or more, even more preferably 15 or more to improve the ester compound in heat resistance and hydrolysis resistance and heighten the compound in kinetic viscosity. In order to lower the kinetic viscosity, the number is preferably 19 or less, more preferably 18 or less, even more preferably 17 or less.

When $R^5$ is the cycloalkyl group having 5 to 21 (both inclusive) carbon atoms and optionally substituted with an alkyl chain, the number of the carbon atoms therein is preferably 6 or more to improve the ester compound in heat resistance and hydrolysis resistance and heighten the compound in kinetic viscosity. In order to lower the kinetic viscosity, the number is preferably 17 or less, more preferably 11 or less, even more preferably 7 or less.

In the general formula (2): —O—C(=O)—$R^5$, $R^5$ is preferably a linear alkyl group having 5 to 21 (both inclusive) carbon atoms, and is more preferably a linear alkyl group having 5 to 21 (both inclusive) carbon and a branched alkyl group having 9 to 21 (both inclusive) carbon atoms.

$R^5$ is preferably the branched alkyl group having 9 to (both inclusive) carbon atoms, and the cycloalkyl group having 5 to 21 (both inclusive) carbon atoms and optionally substituted with an alkyl chain.

For the ester compound, the following may be appropriately used as an ester compound other than any compound represented by the general formula (1) to adjust the viscosity or give other advantageous effects thereto: for example, natural fats and oils, such as palm oil, monoesters such as a higher aliphatic acid methyl ester, diesters such as dioctyl sebacate, and other ester compounds.

Hereinafter, a description will be made about the content or the blend amount of each of components in the present invention.

When at least one of $R^1$ to $R^4$ is the general formula (2): —O—C(=O)—$R^5$ in the compound(s) represented by the general formula (1), the ratio by mole of the general formula (2): —O—C(=O)—$R^5$ (hereinafter referred to as (a)) to the whole of the benzoyloxy and the naphthoyloxy groups (hereinafter referred to as (b)) (ratio (a)/(b)) is preferably 0.1 or more, more preferably 1 or more, even more preferably 1.5 or more to lower each of the ester compounds in kinetic viscosity. The ratio is preferably 10 or less, more preferably 5 or less, even more preferably 3 or less to improve the ester compound in heat resistance.

When $R^5$ is the linear alkyl group having 5 to 21 (both inclusive) carbon atoms in the compound(s) represented by the general formula (1), the ratio by mole of the linear alkyl group having 5 to 21 (both inclusive) carbon atoms (hereinafter referred to as (c)) to the whole of the benzoyloxy and naphthoyloxy groups (ratio (c)/(b)) is preferably 0.1 or more, more preferably 0.3 or more, even more preferably 0.5 or more, even more preferably 1 or more to improve the ester compound in heat resistance and lower the compound in kinetic viscosity. To heighten the ester compound in kinetic viscosity, the ratio is preferably 10 or less, more preferably 6 or less, even more preferably 5 or less, even more preferably 4 or less, even more preferably 3 or less, even more preferably 2 or less.

When $R^5$ is the linear alkyl group having 5 to 21 (both inclusive) carbon atoms and the branched alkyl group having 9 to 21 (both inclusive) carbon atoms, the ratio by mole of the linear alkyl group having 5 to 21 (both inclusive) carbon atoms (c) to the branched alkyl group having 9 to 21 (both inclusive) carbon atoms (hereinafter referred to as (d)) (ratio (c)/(d)) is preferably 0.1 or more, more preferably 0.5 or more, even more preferably 1 or more to lower the ester compound in kinetic viscosity. To improve the ester compound in heat resistance and heighten the compound in kinetic viscosity, the ratio is preferably 10 or less, more preferably 6 or less, even more preferably 5 or less, even more preferably 4 or less, even more preferably 3 or less, even more preferably 2 or less.

When $R^5$ is the branched alkyl group having 9 to 21 (both inclusive) carbon atoms and the cycloalkyl group having 5 to 21 (both inclusive) carbon atoms and optionally substituted with an alkyl chain, the ratio by mole of the branched alkyl group having 9 to 21 (both inclusive) carbon atoms (d) to the cycloalkyl group having 5 to 21 (both inclusive) and optionally substituted with the alkyl chain (hereinafter referred to as (e)) (ratio (d)/(e)) is preferably 0.1 or more, more preferably 0.2 or more, even more preferably 0.3 or more to heighten the ester compound in kinetic viscosity. To improve the ester compound in heat resistance, the ratio is preferably 10 or less, more preferably 5 or less, even more preferably 3 or less, even more preferably 2 or less.

The mixture includes a compound in which at least one of $R^1$ to $R^4$ is the general formula (2): —O—C(=O)—$R^5$. In the mixture, the proportion of a compound in which at least one of $R^1$ to $R^4$ is a benzoyloxy or naphthoyloxy group is from 5 to 100% by mole both inclusive. In the mixture, the proportion of this compound, in which at least one of $R^1$ to $R^4$ is a benzoyloxy or naphthoyloxy group, is 25% or more by mole, more preferably 35% or more by mole, even more preferably 40% or more by mole to heighten the ester compound in kinetic viscosity. In order to improve the ester compound in heat resistance and lower the compound in kinetic viscosity, the proportion in the mixture is preferably 99% or less by mole, more preferably 95% or less by mole, even more preferably 90% or less by mole, even more preferably 80% or less by mole, even more preferably 70% or less by mole.

In the mixture, the proportion by mass of the proportion of the compound, in which at least one of $R^1$ to $R^4$ is a benzoyloxy or naphthoyloxy group, is preferably 25% or more by mass, more preferably 30% or more by mass, even more preferably 35% or more by mass, even more preferably 40% or more by mass to heighten the ester compound in kinetic viscosity. In order to improve the ester compound in heat resistance and lower the kinetic viscosity, the proportion in the mixture is preferably 100% or less by mass, more preferably 95% or less by mass, even more preferably 90% or less by mass, even more preferably 80% or less by mass, even more preferably 70% or less by mass.

The proportion by mass of the mixture in the lubricant base oil is preferably from 50 to 100% by mass both inclusive, more preferably 60% or more by mass, even more preferably 70% or more by mass, even more preferably 80% or more by mass, even more preferably 90% or more by mass, even more preferably 100% by mass to improve the ester compound in heat resistance, lubricity and hydrolysis resistance.

Method for Producing Ester Compounds

About the ester compounds in the present invention, a producing method thereof is not limited. The ester compounds can be usually produced by subjecting one or more alcohols and one or more carboxylic acids to esterification reaction in a known manner.

Alcohol(s)

The alcohol(s) include(s) a polyhydric alcohol represented by the following general formula (3):

[Formula 4]

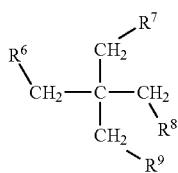

(3)

wherein $R^6$ to $R^9$ each independently represent a hydrogen atom, a methyl group, or a hydroxyl group, and at least two of $R^6$ to $R^9$ are each a hydroxyl group.

About $R^6$ to $R^9$ in the general formula (3), at least two of $R^6$ to $R^9$ are each a hydroxyl group, and three or more thereof are each preferably a hydroxyl group. Examples of the polyvalent alcohol include pentaerythritol, trimethylolpropane, trimethylolethane, and neopentyl glycol. The polyhydric alcohol is preferably pentaerythritol, trimethylolpropane, or neopentyl glycol to improve each of the ester compounds in heat resistance and hydrolysis resistance. Trimethylolpropane is preferred to lower the ester compound in pour point, and further pentaerythritol is preferred to improve the ester compound in heat resistance.

About the above-mentioned alcohol(s), various monohydric alcohols or polyols are each appropriately usable as an alcohol component other than the polyhydric alcohol. The number of carbon atoms in each of the monohydric alcohols is usually from 1 to 24. The carbon chain thereof may be a linear or branched chain. The monohydric alcohol may be saturated or unsaturated. The polyols are each usually a polyol having 2 to 10 valences.

Examples of the polyols include ethylene glycol, diethylene glycol, polyethylene glycol, propylene glycol, dipropylene glycol, polypropylene glycol, 1,3-propanediol, 1,2-propanediol, 1,3-butanediol, 1,4-butanediol, 2-methyl-1,2-propanediol, 2-methyl-1,3-propanediol, 1,2-pentanediol, 1,3-pentanediol, 1,4-pentanediol, 1,5-pentanediol, and other diols; 1,2,4-butanetriol, 1,3,5-pentanetriol, 1,2,6-hexanetriol, and other triol compounds; dipentaerythritol, tripentaerythritol, and other multimers of trimethylolalkanes; glycerol, diglycerol, triglycerol, tetraglycerol, and other polyglycerols; sorbitol, sorbitan, sorbitol glycerin condensates, adonitol, arabitol, xylitol, mannitol, xylose, arabinose, ribose, rhamnose, glucose, fructose, galactose, mannose, sorbose, cellobiose, maltose, isomaltose, trehalose, sucrose, and other saccharides.

Carboxylic Acid(s)

The carboxylic acid(s) include(s) one or more aromatic carboxylic acids and one or more aliphatic carboxylic acids. The aromatic carboxylic acid(s) include(s) benzoic acid and/or naphthoic acid, and the aliphatic carboxylic acid(s) include(s) at least one monocarboxylic acid selected from linear alkyl aliphatic acid each having 6 to 22 (both inclusive) carbon atoms, branched alkyl aliphatic acids each having 10 to 22 (both inclusive) carbon atoms and cycloalkanecarboxylic acids each having 6 to 22 (both inclusive) carbon atoms and optionally substituted with an alkyl chain.

In order to heighten the ester compound in kinetic viscosity, the aromatic carboxylic acid(s) is/are preferably benzoic acid, 1-naphthoic acid, and/or 2-naphthoic acid.

Examples of the linear alkyl aliphatic acids each having 6 to 22 (both inclusive) carbon atoms include n-hexanoic acid, n-heptanoic acid, n-octanoic acid, n-nonanoic acid, n-decanoic acid, n-dodecanoic acid, n-tetradecanoic acid, n-pentadecanoic acid, n-hexadecanoic acid, n-heptadecanoic acid, n-octadecanoic acid, n-icosanoic acid, and n-docosanoic acid. Out of these examples, preferred are n-heptanoic acid, n-octanoic acid, and n-nonanoic acid to realize a decrease of the lubricant oil composition in torque, and make the filling-work thereof effective.

About each of the linear alkyl aliphatic acids each having 6 to 22 (both inclusive) carbon atoms, the number of carbon atoms therein is preferably 7 or more, more preferably 8 or more, even more preferably 9 or more to improve the ester compound in heat resistance and hydrolysis resistance. The number is preferably 18 or less, more preferably 12 or less, even more preferably 10 or less to lower the ester compound in kinetic viscosity.

Examples of the branched alkyl aliphatic acids each having 10 to 22 (both inclusive) carbon atoms include branched aliphatic acids in each of which a methyl branch has been formed by synthesis using, as a raw material, a linear unsaturated aliphatic acid derived from natural fats and oils, and synthesized aliphatic acids each derived from a polyolefin having a branched chain and yielded by polymerizing 1-butene or any other alkene as a raw material. An alkyl aliphatic acid having 10 to 22 (both inclusive) carbon atoms and having a branched chain is usable without any restriction. Examples of the branched alkyl aliphatic acids each having 10 to 22 (both inclusive) carbon atoms include 13-methyltetradecanoic acid, 12-methyltetradecanoic acid, 15-methylhexadecanoic acid, 14-methylhexadecanoic acid, 10-methylhexadecanoic acid, 2-hexyldecanoic acid, isopalmitic acid, isostearic acid, isoarachic acid, phytanic acid. Out of these examples, isostearic acid is preferred to improve the ester compound in heat resistance and hydrolysis resistance.

About each of the branched alkyl aliphatic acids each having 10 to 22 (both inclusive) carbon atoms, the number of carbon atoms therein is preferably 12 or more, more preferably 14 or more, even more preferably 16 or more to improve the ester compound in heat resistance and hydrolysis resistance and heighten the compound in kinetic viscosity. The number is preferably 20 or less, more preferably 19 or less, even more preferably 18 or less to lower the ester compound in kinetic viscosity.

Examples of the cycloalkanecarboxylic acids each having 6 to 22 (both inclusive) carbon atoms and optionally substituted with an alkyl chain include cyclopropanecarboxylic acid, cyclobutanecarboxylic acid, cyclopentanecarboxylic acid, cyclohexanecarboxylic acid, cycloheptanecarboxylic acid, methylcyclohexanecarboxylic acid, 4-t-butylcyclohexanecarboxylic acid, and dodecylcyclohexanecarboxylic acid. Out of these examples, cyclohexanecarboxylic acid is preferred to improve the ester compound in heat resistance and hydrolysis resistance.

About each of the cycloalkanecarboxylic acids each having 6 to 22 (both inclusive) carbon atoms and optionally substituted with an alkyl chain, the number of carbon atoms therein is preferably 7 or more to improve the ester compound in heat resistance and hydrolysis resistance and heighten the compound in kinetic viscosity. The number is preferably 18 or less, more preferably 12 or less, even more preferably 8 or less to lower the ester compound in kinetic viscosity.

In order to improve the ester compound in heat resistance and hydrolysis resistance, the above-mentioned carboxylic acid(s) preferably include(s) one or more of the linear alkyl aliphatic acids each having 6 to 22 (both inclusive) carbon atoms, out of the above-mentioned aliphatic carboxylic acids; and more preferably include(s) one or more of the linear alkyl aliphatic acids each having 6 to 22 (both inclusive) carbon atoms and one or more of the branched alkyl aliphatic acids each having 10 to 22 carbon atoms, or preferably include(s) one or more of the branched alkyl aliphatic acids each having 10 to 22 (both inclusive) carbon atoms and one or more of the cycloalkanecarboxylic acids each having 6 to 22 (both inclusive) carbon atoms and optionally substituted with an alkyl chain.

For the carboxylic acid(s), as a carboxylic acid other than the aromatic carboxylic acid(s) and the aliphatic carboxylic acid(s), a carboxylic acid compound that may be of various types (hereinafter referred to as a different carboxylic acid compound) may be appropriately used. Examples of the different carboxylic acid compound include valeric acid, 2-methylvaleric acid, 4-methylvaleric acid, 2-methylhexanoic acid, 5-methylhexanoic acid, 4,4-dimethylpentanoic acid, 2-methyheptanoic acid, 2-ethylhexanoic acid, 2,2-dimethylhexanoic acid, and 3,5,5-trimethylhexanoic acid.

Hereinafter, a description will be made about the blend amount of each of components in the method of the present invention for producing ester compounds.

In the alcohol(s), the proportion of the polyhydric alcohol represented by the general formula (2) is preferably 80% or more by mole, more preferably 90% or more by mole, even more preferably 95% or more by mole, even more preferably 98% or more by mole, even more preferably 100% by mole.

In the carboxylic acid(s), the proportion of the aromatic carboxylic acid(s) is preferably from 10 to 90% by mole both inclusive to improve the ester compound in heat resistance and hydrolysis resistance. The proportion of the aromatic carboxylic acid(s) in the carboxylic acid(s) is more preferably 15% or more by mole, more preferably 20% or more by mole to improve the ester compound in heat resistance and heighten the compound in kinetic viscosity. The proportion is more preferably 80% or less by mole, even more preferably 70% or less by mole, even more preferably 60% or less to lower the ester compound in kinetic viscosity.

When the carboxylic acid(s) include(s), as the aliphatic carboxylic acid(s), one or more of the linear alkyl aliphatic acids each having 6 to 22 (both inclusive) carbon atoms, the proportion of the linear alkyl aliphatic acid(s) having 6 to 22 (both inclusive) carbon atoms in the carboxylic acid(s) is preferably from 10 to 80% by mole both inclusive to improve the ester compound in heat resistance and hydrolysis resistance. The proportion of the linear alkyl aliphatic acid(s) having 6 to 22 (both inclusive) carbon atoms is more preferably 15% or more by mole, even more preferably 20% or more by mole, even more preferably 30% or more by mole to improve the ester compound in heat resistance and lower the compound in kinetic viscosity. The proportion is more preferably 80% or less by mole, even more preferably 70% or less by mole, even more preferably 60% or less by mole, even more preferably 55% or less by mole to heighten the ester compound in kinetic viscosity.

When the carboxylic acid(s) include(s), as the aliphatic carboxylic acid(s), one or more of the branched alkyl aliphatic acids each having 10 to 22 (both inclusive) carbon atoms, the proportion of the branched alkyl aliphatic acid(s) having 10 to 22 (both inclusive) carbon atoms in the carboxylic acid(s) is preferably from 10 to 50% by mole both inclusive to improve the ester compound in heat resistance and hydrolysis resistance. The proportion of the branched alkyl aliphatic acid(s) having 10 to 22 (both inclusive) carbon atoms is more preferably 15% or more by mole, even more preferably 20% or more by mole to improve the ester compound in heat resistance and heighten the compound in kinetic viscosity. The proportion is more preferably 50% or less by mole, even more preferably 45% or less by mole, even more preferably 40% or less by mole to lower the ester compound in kinetic viscosity.

When the carboxylic acid(s) include(s), as the aliphatic carboxylic acid(s), one or more of the cycloalkanecarboxylic acids each having 6 to 22 (both inclusive) carbon atoms and optionally substituted with an alkyl chain, the proportion of the cycloalkanecarboxylic acid(s) having 6 to 22 (both inclusive) carbon atoms and optionally substituted with the alkyl chain in the carboxylic acid(s) is preferably from 10 to 70% by mole both inclusive to improve the ester compound in heat resistance and hydrolysis resistance. The proportion of the cycloalkanecarboxylic acid(s) having 6 to 22 (both inclusive) carbon atoms and optionally substituted with the alkyl chain is more preferably 20% or more by mole in the carboxylic acid(s) to improve the ester compound in heat resistance and hydrolysis resistance. The proportion is more preferably 60% or less by mole, even more preferably 55% or less by mole to lower the ester compound in kinetic viscosity.

In order to promote the esterification reaction in the reaction between the alcohol(s) and the carboxylic acid(s), the ratio by equivalent between the two is usually adjusted to set the amount of carboxyl groups of the carboxylic acid component(s) into a range preferably from 1.05 to 1.5 equivalents, more preferably from 1.1 to 1.3 equivalents per equivalent of hydroxyl groups of the alcohol component(s). When the proportion of the carboxyl groups of the carboxylic acid component(s) is made high, the reactivity between the alcohol(s) and the carboxylic acid(s) is made good; however, after the end of the reaction, it is necessary to remove an excessive amount of the carboxylic acid(s). Examples of a method for the removal include reduced-pressure distillation, steaming, and adsorption and removal using an adsorbent.

The amount of carboxyl groups of the aromatic carboxylic acid(s) is preferably from 10 to 90 equivalents both inclusive, more preferably from 20 to 80 equivalents both inclusive, even more preferably from 25 to 75 equivalents both inclusive for 100 equivalents of hydroxyl groups of the polyhydric alcohol represented by the general formula (2).

The amount of carboxyl groups of the aliphatic carboxylic acid(s) is preferably from 60 to 140 equivalents both inclusive, more preferably from 65 to 120 equivalents both inclusive, even more preferably from 70 to 100 equivalents both inclusive for 100 equivalents of the hydroxyl groups of the polyhydric alcohol represented by the general formula (2).

Furthermore, the amount of the whole of the carboxyl groups of the aromatic carboxylic acid(s) and the aliphatic acid(s) is preferably from 100 to 150 equivalents both inclusive for 100 equivalents of the hydroxyl groups of the polyhydric alcohol represented by the general formula (2).

In one embodiment of the present invention, it is preferred that the polyhydric alcohol represented by the general formula (2) is at least one selected from pentaerythritol, trimethylolpropane, and neopentyl glycol, and the carboxylic acid(s) is/are the aromatic carboxylic acid(s), one or more of the branched alkyl aliphatic acids each having 10 to 22 (both inclusive) carbon atoms, and enantoic acid (n-heptanoic acid) or cyclohexanecarboxylic acid. It is more preferred that the polyhydric alcohol is pentaerythritol, and the carboxylic acid(s) is/are benzoic acid, one or more branched alkyl aliphatic acids each having 16 to 20 (both inclusive) carbon atoms, and enantoic acid or cyclohexanecarboxylic acid.

About the condensed esters in the present invention, the 40° C. kinetic viscosity thereof, which will be detailed later, is preferably 30 mm²/s or more, more preferably 40 mm²/s or more, and is preferably 1500 mm²/s or less, more preferably 200 mm²/s or less to keep the lubricity of the lubricant base oil certainly at low temperatures. About the condensed esters in the present invention, the 100° C. kinetic viscosity thereof, which will be detailed later, is preferably 5 mm²/s or more, more preferably 6 mm²/s or more, and is preferably 30 mm²/s or less, more preferably 20 mm²/s or less to keep the lubricity of the lubricant base oil certainly at high temperatures.

About the condensed esters in the present invention, the pour point thereof, which will be detailed later, is preferably −20° C. or lower, more preferably −30° C. or lower, even more preferably −40° C. or lower, even more preferably −50° C. or lower to keep the fluidity of the lubricant base oil certainly at low temperatures.

Lubricant Oil Composition

The lubricant oil composition of the present invention includes the above-defined lubricant base oil. About the proportion by mass of the lubricant base oil in the lubricant oil composition of the present invention, the lubricant base oil is sufficient to be contained in an amount corresponding to performance required in accordance with a use article of the composition. From the viewpoint of an improvement of the composition in heat resistance and the lubricity thereof, the proportion is preferably from 50 to 100% by mass both inclusive, more preferably 60% or more by mass, even more preferably 70% or more by mass, even more preferably 80% or more by mass, even more preferably 90% or more by mass, even more preferably 100% by mass.

As required, other additives may be blended into the lubricant oil composition as far as the advantageous effects of the present invention are not damaged. Examples of the other additives include a detergent, a dispersant, an antioxidant, an oiliness improver, an antiwear agent, an extreme pressure agent, a rust inhibitor, a corrosion inhibitor, a metal deactivator, a viscosity index improver, a pour point depressant, an antifoaming agent, an emulsifier, a demulsifier, an anti-mold agent, and a solid lubricant.

The total blend amount of the other additives is usually 10 parts or less by mass, preferably 5 parts or less by mass for 100 parts by mass of the lubricant oil composition.

The lubricant oil composition of the present invention is usable for gasoline engine oil, diesel engine oil, marine engine oil, and other combustion lubricant oils; and gear oil, automatic transmission oil, hydraulic oil, fire-resistant hydraulic fluid, refrigerator oil, compressor oil, vacuum pump oil, bearing oil, insulating oil, turbine oil, sliding surface oil, rock drill oil, metal working oil, plastic working oil, heat treatment oil, grease, and other non-combustion type lubricant oils. The lubricant oil composition of the present invention is also usable for sliding parts, such as rotating and sliding parts as a sliding bearing, plane sliding parts such as a thrust bearing, and sliding parts such as a spline; and is usable for a method for lubricating a spline section of a clutch disc, a shaft and a gear-inside-diameter bearing section of a transmission, a spline section of a hub-sleeve, a section supported by a metal in each section, and a spline section of a change operating system.

In connection with the above-mentioned embodiments, the present document DESCRIPTION discloses the following lubricant base oil, and lubricant oil composition including the lubricant base oil:

<1> A lubricant base oil, including an ester compound, wherein: the ester compound includes a mixture including one or more compounds (each) represented by the following general formula (1):

[Formula 5]

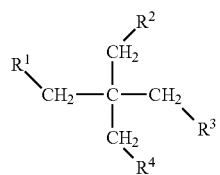

(1)

wherein $R^1$ and $R^2$ each independently represent a hydrogen atom, a methyl group, a benzoyloxy group, a naphthoyloxy group or a general formula (2): —O—C(=O)—$R^5$, and $R^3$ and $R^4$ each independently represent a benzoyloxy group, a naphthoyloxy group or the general formula (2): —O—C(=O)—$R^5$ wherein $R^5$ represents a linear alkyl group having 5 to 21 (both inclusive) carbon atoms, a branched alkyl group having 9 to 21 (both inclusive) carbon atoms, or a cycloalkyl group having 5 to 21 (both inclusive) carbon atoms and optionally substituted with an alkyl chain; the mixture includes a compound about which at least one of $R^2$ to $R^4$ is the general formula (2):—O—C(=O)—$R^5$; and a proportion of a compound about which at least one of $R^1$ to $R^4$ is the benzoyloxy group or the naphthoyloxy group in the mixture is from 5 to 100% by mole both inclusive.

<2> The lubricant base oil according to item <1>, wherein when $R^5$ is the linear alkyl group having 5 to 21 (both inclusive) carbon atoms, the number of the carbon atoms therein is preferably 6 or more, more preferably 7 or more, even more preferably 8 or more, and is preferably 17 or less, more preferably 11 or less, even more preferably 9 or less.

<3> The lubricant base oil according to item <1>, wherein when $R^5$ is the branched alkyl group having 9 to 21 (both inclusive) carbon atoms, the number of the carbon atoms therein is preferably 11 or more, more preferably 13 or more, even more preferably 15 or more, and is preferably 19 or less, more preferably 18 or less, even more preferably 17 or less.

<4> The lubricant base oil according to item <1>, wherein when $R^5$ is the cycloalkyl group having 5 to 21 (both inclusive) carbon atoms and optionally substituted with an allyl chain, the number of the carbon atoms therein is preferably 6 or more, and is preferably 17 or less, more preferably 11 or less, even more preferably 7 or less.

<5> The lubricant base oil according to any one of items <1> to <3>, wherein $R^5$ is preferably the linear alkyl group having 5 to 21 (both inclusive) carbon atoms, more preferably the linear alkyl group having 5 to 21 (both inclusive) carbon atoms and the branched alkyl group having 9 to 21 (both inclusive) carbon atoms.

<6> The lubricant base oil according to item <1>, wherein $R^5$ is preferably the branched alkyl group having 9 to 21 (both inclusive) carbon atoms and the cycloalkyl group having 5 to 21 (both inclusive) carbon atoms and optionally substituted with the alkyl chain.

<7> The lubricant base oil according to item <1>, wherein the ratio by mole of the general formula (2): —O—C(=O)—$R^5$ (hereinafter referred to as (a)) to the whole of the benzoyloxy and naphthoyloxy groups (hereinafter referred to as (b)) (ratio (a)/(b)) is preferably 0.1 or more, more preferably 1 or more, even more preferably 1.5 or more, and is preferably 10 or less, more preferably 5 or less, even more preferably 3 or less.

<8> The lubricant base oil according to item <1>, wherein when $R^5$ is the linear alkyl group having 5 to 21 (both inclusive) carbon atoms, the ratio by mole of the linear alkyl group having 5 to 21 (both inclusive) carbon atoms (hereinafter referred to as (c)) to the whole (b) of the benzoyloxy and naphthoyloxy groups (ratio (c)/(b)) is preferably 0.1 or more, more preferably 0.3 or more, even more preferably 0.5 or more, even more preferably 1 or more, and is preferably 10 or less, more preferably 6 or less, even more preferably 5 or less, even more preferably 4 or less, even more preferably 3 or less, even more preferably 2 or less.

<9> The lubricant base oil according to item <1>, wherein when $R^5$ is the linear alkyl group having 5 to 21 (both inclusive) carbon atoms and the branched alkyl group having 9 to 21 (both inclusive) carbon atoms, the ratio by mole of the linear alkyl group (c) having 5 to 21 (both inclusive) carbon atoms to the branched alkyl group having 9 to 21 (both inclusive) carbon atoms (hereinafter referred to as (d)) (ratio (c)/(d)) is preferably 0.1 or more, more preferably 0.5 or more, even more preferably 1 or more, and is preferably 10 or less, more preferably 6 or less, even more preferably 5 or less, even more preferably 4 or less, even more preferably 3 or less, even more preferably 2 or less.

<10> The lubricant base oil according to item <1>, wherein when $R^5$ is the branched alkyl group (d) having 9 to (both inclusive) carbon atoms and the cycloalkyl group having 5 to 21 (both inclusive) carbon atoms and optionally substituted with the alkyl chain, the ratio by mole of the branched alkyl group (d) having 9 to 21 (both inclusive) carbon atoms to the cycloalkyl group having 5 to 21 (both inclusive) carbon atoms and optionally substituted with the alkyl chain (hereinafter referred to as (e)) (ratio (d)/(e)) is preferably 0.1 or more, more preferably 0.2 or more, even more preferably 0.3 or more, and is preferably 10 or less, more preferably 5 or less, even more preferably 3 or less, even more preferably 2 or less.

<11> The lubricant base oil according to item <1>, wherein in the mixture, the proportion of the compound in which at least one of $R^1$ to $R^4$ is a benzoyloxy or naphthoyloxy group is preferably 25% or more by mole, more preferably 35% or more by mole, even more preferably 40% or more by mole, and is preferably 99% or less by mole, more preferably 95% or less by mole, even more preferably 90% or less by mole, even more preferably 80% or less by mole, even more preferably 70% or less by mole.

<12> The lubricant base oil according to item <1>, wherein in the mixture, the proportion by mass of the compound in which at least one of $R^1$ to $R^4$ is a benzoyloxy or naphthoyloxy group is preferably 25% or more by mass, more preferably 30% or more by mass, even more preferably 35% or more, even more preferably 40% or more by mass, and is preferably 100% or less by mass, more preferably 95% or less by mass, even more preferably 90% or less by mass, even more preferably 80% or less by mass, even more preferably 70% or less by mass.

<13> The lubricant base oil according to item <1>, wherein the proportion by mass of the mixture is preferably from 50 to 100% by mass both inclusive, more preferably 60% or more by mass, even more preferably 70% or more by mass, even more preferably 80% or more by mass, even more preferably 90% or more by mass, even more preferably 100% by mass.

<14> The lubricant base oil according to item <1>, wherein the proportion by mass of the ester compounds is preferably from 50 to 100% by mass both inclusive, more preferably 60% or more by mass, even more preferably 70% or more by mass, even more preferably 80% or more by mass, even more preferably 90% or more by mass, even more preferably 100% by mass.

<15> A method for producing the lubricant base oil recited in any one of items <1> to <14> including the step of producing a mixture including one or more compounds (each) yielded by condensing one or more alcohols and one or more carboxylic acids, and (each) represented by the general formula (1); wherein the alcohol(s) include(s) a polyhydric alcohol represented by the following general formula (3):

[Formula 6]

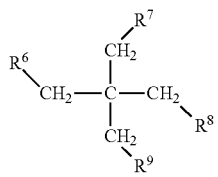

(3)

wherein $R^6$ to $R^9$ each independently represent a hydrogen atom, a methyl group or a hydroxyl group, and further at least two of $R^6$ to $R^9$ each represent the hydroxyl group; the carboxylic acid(s) include(s) one or more aromatic carboxylic acids and one or more aliphatic acids; the aromatic carboxylic acid(s) includes(s) benzoic acid and/or naphthoic acid; and the aliphatic carboxylic acid(s) include(s) at least one monocarboxylic acid selected from linear alkyl aliphatic acids each having 6 to (both inclusive) carbon atoms, branched alkyl aliphatic acids each having 10 to 22 (both inclusive) carbon atoms, and cycloalkanecarboxylic acids each having 6 to 22 (both inclusive) carbon atoms and each optionally substituted with an alkyl chain.

<16> The method according to item <15> for producing the lubricant base oil, wherein the polyhydric alcohol is preferably pentaerythritol, trimethylolpropane, or neopentyl glycol, more preferably trimethylolpropane or pentaerythritol.

<17> The method according to item <15> or <16> for producing the lubricant base oil, wherein (each of) the aromatic carboxylic acid(s) is preferably benzoic acid, 1-naphthoic acid, or 2-naphthoic acid.

<18> The method according to any one of items <15> to <17> for producing the lubricant base oil, wherein about each of the linear alkyl aliphatic acids each having 6 to (both inclusive) carbon atoms, the number of the carbon atoms therein is preferably 7 or more, more preferably 8 or more, even more preferably 9 or more, and is preferably 18 or less, more preferably 12 or less, even more preferably 10 or less.

<19> The method according to any one of items <15> to <17> for producing the lubricant base oil, wherein about each of the branched alkyl aliphatic acids each having 10 to 22 (both inclusive) carbon atoms, the number of the carbon atoms therein is preferably 12 or more, more preferably 14 or more, even more preferably 16 or more, and is preferably 20 or less, more preferably 19 or less, even more preferably 18 or less.

<20> The method according to any one of items <15> to <17> for producing the lubricant base oil, wherein about each of the cycloalkanecarboxylic acids each having 6 to 22 (both inclusive) carbon atoms and each optionally substituted with the alkyl chain, the number of the carbon atoms therein is preferably 7 or more, and is preferably 18 or less, more preferably 12 or less, even more preferably 8 or less.

<21> The method according to any one of items <15> to <20> for producing the lubricant base oil, wherein the proportion of the polyhydric alcohol represented by the general formula (2) in the alcohol(s) is preferably 80% or more by mole, more preferably 90% or more by mole, more preferably 95% or more by mole, even more preferably 98% or more by mole, even more preferably 100% by mole.

<22> The method according to any one of items <15> to <21> for producing the lubricant base oil, wherein the proportion of the aromatic carboxylic acid(s) in the carboxylic acid(s) is preferably from 10 to 90% by mole both inclusive, more preferably 15% or more by mole, even more preferably 20% or more by mole, and is more preferably 80% or less by mole, even more preferably 70% or less by mole, even more preferably 60% or less by mole.

<23> The method according to any one of items <15> to <17> for producing the lubricant base oil, wherein when the carboxylic acid(s) include(s) one or more of the linear alkyl aliphatic acids each having 6 to 22 (both inclusive) carbon atoms as the aliphatic carboxylic acid(s), the proportion of the linear alkyl aliphatic acid(s) having 6 to 22 (both inclusive) carbon atoms in the carboxylic acid(s) is from 10 to 80% by mole, more preferably 15% or more by mole, even more preferably 20% or more by mole, even more preferably 30% or more by mole, and is more preferably 80% or less by mole, even more preferably 70% or less by mole, even more preferably 60% or less by mole, even more preferably 55% or less by mole.

<24> The method according to any one of items <15> to <17> for producing the lubricant base oil, wherein when the carboxylic acid(s) include(s) one or more of the branched alkyl aliphatic acids each having 10 to 22 (both inclusive) carbon atoms as the aliphatic carboxylic acid(s), the proportion of the branched alkyl aliphatic acid(s) having 10 to 22 (both inclusive) carbon atoms in the carboxylic acid(s) is from 10 to 50% by mole, more preferably 15% or more by mole, even more preferably 20% or more by mole, and is more preferably 50% or less by mole, even more preferably 45% or less by mole, even more preferably 40% or less by mole.

<25> The method according to any one of items <15> to <17> for producing the lubricant base oil, wherein when the carboxylic acid(s) include(s) one or more of the cycloalkanecarboxylic acids each having 6 to 22 (both inclusive) carbon atoms and optionally substituted with the alkyl chain as the aliphatic carboxylic acid(s), the proportion of the cycloalkanecarboxylic acid(s) having 6 to (both inclusive) carbon atoms and optionally substituted with the alkyl chain is from 10 to 70% by mole, more preferably 20% or more by mole, and is more preferably 60% or less by mole, even more preferably 55% or less by mole.

<26> The method according to any one of items <15> to <25> for producing the lubricant base oil, wherein for 100 equivalents of hydroxyl groups of the polyhydric alcohol, the amount of carboxyl groups of the aromatic carboxylic acid(s) is from 10 to 90 equivalents both inclusive, more preferably from 20 to 80 equivalents both inclusive, even more preferably from 25 to 75 equivalents both inclusive.

<27> The method according to any one of items <15> to <26> for producing the lubricant base oil, wherein for 100 equivalents of hydroxyl groups of the polyhydric alcohol, the amount of carboxyl groups of the aliphatic carboxylic acid(s) is from 60 to 140 equivalents both inclusive, more preferably from 65 to 120 equivalents both inclusive, even more preferably from 70 to 100 equivalents both inclusive.

<28> The method according to any one of items <15> to <27> for producing the lubricant base oil, wherein for 100 equivalents of hydroxyl groups of the polyhydric alcohol, the amount of the whole carboxyl groups of the aromatic carboxylic acid(s) and the aliphatic carboxylic acid(s) is from 100 to 150 equivalents both inclusive.

<29> A lubricant oil composition including the lubricant base oil recited in any one of items <1> to <14>.

<30> Use of the lubricant oil composition recited in item <29> for a sliding part.

<31> A lubricating method, using the lubricant oil composition recited in item <29>.

EXAMPLES

Hereinafter, the present invention will be described in more detail by way of working examples thereof. However, the invention is not limited only to these working examples.

Example 1

Synthesis of Ester Compounds

Into a 1-L four-necked flask equipped with a stirrer, a thermometer, a nitrogen-blowing tube and a condenser were added 378.6 g of enantoic acid (n-heptanoic acid), and 118.3 g of benzoic acid as carboxylic acids, and then thereto was added 110.0 g of pentaerythritol as an alcohol. The addition amount of the carboxylic acids was adjusted to set the amount of all carboxyl groups of the carboxylic acids to 1.2 equivalents per equivalent of hydroxyl groups of the alcohol.

Next, nitrogen gas was blown into the flask. While the reaction system was stirred, the temperature thereof was raised to 250° C. The system was kept at 250° C. for 18 hours. The condenser was used to remove water distilled off therefrom to the outside of the flask. After the end of the reaction, an excess of the carboxylic acid components was distilled off under a reduced pressure of 0.13 kPa. Under the reduced pressure of 0.13 kPa, the system was subjected to steaming for one hour to cause remaining fractions of the carboxylic acid components to be adsorbed on an adsorbent (trade name: KYOWAAD 500SH, manufactured by Kyowa Chemical Industry Co., Ltd.). Thereafter, the production system was filtrated to yield ester compounds in Example 1. About the resultant ester compounds, evaluations described below were obtained. The evaluation results are shown in Table 1.

Evaluation of Respective Proportions of Components in Ester Compounds

The respective component proportions (% by mole) of the ester compounds yielded as described above were measured by a method described below.

The resultant ester compounds were dissolved in deuterium chloroform. A nuclear magnetic resonance machine (trade name: system Agilent 400-MR DD2, manufactured by the company Agilent Technologies) was used to make a $^1$H-NMR measurement of the solution. On the basis of proton intensities of peaks originating from ester groups, which made their appearance near 4 ppm, the percentage by mole of each of the respective numbers of ester groups each having in the molecule thereof an aromatic ring was calculated out. On the basis of the number of the ester groups in the molecule, peaks thereof, the number of which is "the number of the ester groups"בin"2", make their appearance. When the number is, for example, 4, peaks originating from 0, 1, 2, 1, 3, 2, 3 and 4 groups make their appearance toward lower values in the magnetic field. When the number is 3, peaks originating from 0, 1, 2, 1, 2, and 3 groups make their appearance toward lower values in the magnetic field. When the number is 2, peaks originating from 0, 1, 1, and 2 groups make their appearance toward lower values in the magnetic field. The intensity of protons is in proportional to the number of moles thereof. Thus, from the proportion of the proton intensity of each of the peaks gained in the measurement, the % by mole of each of the respective numbers of the ester groups each having an aromatic ring was calculated out.

The total component proportion (% by mass) of compounds each having a benzoyloxy or naphthoyloxy group in the mixture of the ester compounds yielded as described above was calculated out by gaining the theoretical molecular weights of each of the resultant ester compounds from the charge ratio between the used alcohols and carboxylic acids, and then using the component proportion (% by mole) of each of the ester compounds.

Evaluation of Hydrolysis Resistance

In an evaluation of the hydrolysis resistance of the ester compounds yielded as described, 10 mL of a 2% by mass of sodium hydroxide in water and 10 mL of the ester compounds were added to a 25-mL test tube with a screw cap. The screw cap was tightened. The test tube was turned upside down three times to mix the water phase and the oil phase preliminarily with each other, and then shaken upward and downward with a shaking-width of about 30 cm 30 times in one minute. After the shaking, the test tube was allowed to stand still, and the inside of the test tube was observed after 5 minutes and 10 minutes. The sample was evaluated in accordance with a criterion described below.

According to this test, the superiority or inferiority of the hydrolysis resistance of the sample is understood in accordance with the following mechanism: The matter that the interface between the water phase and the oil phase is emulsified so that the boundary becomes unclear is to demonstrate that in a short time, the sample is hydrolyzed to produce a soap, or that the sample is easily mixed with water to be easily hydrolyzed. Accordingly, evaluation 1, in which after the shaking, the sample is immediately separated into the two phases, shows excellent hydrolysis resistance.

1: Within 5 minutes, the boundary between the water phase and the oil phase is clear, and these phases are each separated into a volume of 10 mL.

2: In a time of 5 to 10 minutes, the boundary between the water phase and the oil phase becomes clear, and these phases are each separated into a volume of 10 mL.

3: Even when 10 minutes or longer elapse, the boundary between the water phase and the oil phase does not become clear.

Evaluation of Heat Resistance

In an evaluation of the heat resistance of the sample, a differential thermo-gravity simultaneously-measuring device (trade name: TG/DTA6200, manufactured by Seiko Instruments Inc.) was used to raise the temperature of the sample from 35° C. to 550° C. at 10° C./minute in a 250-mL/minute nitrogen-air atmosphere. Under conditions that the sample was kept at the temperature of 550° C. for 10 minutes, the thermal response of the ester compounds was measured, and the residual percentage (% by mass) thereof was calculated out in accordance with an expression described below. It is demonstrated that as the residual percentage is larger, the heat resistance is better.

residual percentage (% by mass)="the mass of the sample at 350° C."/"the mass thereof at 35° C."×100    Expression:

Evaluation of Kinetic Viscosity

In an evaluation of the kinetic viscosity of the sample, the 40° C. kinetic viscosity and the 100° C. kinetic viscosity (mm$^2$/s) thereof were measured, using a Stabinger kinetic viscometer (trade name: SVM3000, manufactured by Anton Paar GmbH) satisfying a precision required in ASTM D7042.

Evaluation of Pour Point

In an evaluation of the pour point of the sample, the pour point (° C.) was measured by a measuring method according to JIS K2269.

Examples 2 to 16, and Comparative Examples 1 to 3>

In each of the examples, ester compounds were prepared and evaluated in the same way as in Example 1 except that the species and the blend amounts of the individual raw materials were changed as shown in Table 1. The evaluation results are shown in Table 1.

TABLE 1

| | | Charged components | | | | | | | | | | | | | |
|---|---|---|---|---|---|---|---|---|---|---|---|---|---|---|---|
| | | Carboxylic acids (% by mole) | | | | | | | | | | Carboxylic acids (% by mass) | | | |
| | | Aromatic carboxylic acids | | | Aliphatic carboxylic acids | | | | | Others | | | Aromatic carboxylic acids | | | Aliphatic carboxylic acids |
| | Alcohol | Ph | α-Naph | β-Naph | nC7 | nC8 | nC9 | iC18 | Cy | nC5 | iC9 | 2EH | Ph | α-Naph | β-Naph | nC7 |
| Example 1 | PET | 25 | | | 75 | | | | | | | | 23.8 | | | 76.2 |
| Example 2 | PET | 25 | | | | 75 | | | | | | | 22.0 | | | |
| Example 3 | PET | 25 | | | | | 75 | | | | | | 20.5 | | | |
| Example 4 | PET | 50 | | | 50 | | | | | | | | 48.4 | | | 51.6 |
| Example 5 | PET | 75 | | | 25 | | | | | | | | 73.8 | | | 26.2 |
| Example 6 | PET | 25 | | | 50 | | | 25 | | | | | 18.3 | | | 39.0 |
| Example 7 | PET | 37.5 | | | 50 | | | 12.5 | | | | | 31.3 | | | 44.4 |
| Example 8 | PET | 12.5 | | | 50 | | | 37.5 | | | | | 8.2 | | | 34.8 |
| Example 9 | PET | 25 | | | 37.5 | | | 37.5 | | | | | 16.4 | | | 26.2 |
| Example 10 | PET | 37.5 | | | 37.5 | | | 25 | | | | | 27.6 | | | 29.5 |
| Example 11 | PET | 12.5 | | | 62.5 | | | 25 | | | | | 9.1 | | | 48.5 |
| Example 12 | PET | 25 | | | 62.5 | | | 12.5 | | | | | 20.7 | | | 55.2 |
| Example 13 | PET | 12.5 | | | | | | 25 | 62.5 | | | | 9.2 | | | |
| Example 14 | TMP | 25 | | | 37.5 | | | 37.5 | | | | | 16.4 | | | 26.2 |
| Example 15 | PET | | 25 | | 37.5 | | | 37.5 | | | | | | 21.7 | | 24.6 |
| Example 16 | PET | | | 25 | 37.5 | | | 37.5 | | | | | | | 21.7 | 24.6 |
| Comparative Example 1 | PET | | | | 100 | | | | | | | | | | | 100 |
| Comparative Example 2 | PET | 25 | | | | | | | | | | 75 | 22.0 | | | |
| Comparative Example 3 | PET | 25 | | | | | | | | 54 | 21 | | 25.7 | | | |

| | Charged components Carboxylic acids (% by mass) | | | | | | | Evaluations Component proportion of each ester compound having one or more benzoyloxy or naphthoyloxy groups (a) in ester compound mixture | | | |
|---|---|---|---|---|---|---|---|---|---|---|---|
| | Aliphatic carboxylic acids | | | | Others | | | % by mole | | | |
| | nC8 | nC9 | iC18 | Cy | nC5 | iC9 | 2EH | No groups (a) | One group (a) | Two groups (a) | Three groups (a) |
| Example 1 | | | | | | | | 31.8 | 40.6 | 20.2 | 6.5 |
| Example 2 | 78.0 | | | | | | | 34.0 | 40.3 | 19.0 | 6.4 |
| Example 3 | | 79.5 | | | | | | 34.4 | 40.5 | 18.4 | 6.4 |
| Example 4 | | | | | | | | 6.3 | 25.2 | 37.9 | 24.7 |
| Example 5 | | | | | | | | 0.5 | 5.1 | 22.4 | 44.2 |
| Example 6 | | | 42.7 | | | | | 35.0 | 43.4 | 19.2 | 2.2 |
| Example 7 | | | 24.3 | | | | | 18.4 | 40.7 | 29.3 | 10.9 |
| Example 8 | | | 57.0 | | | | | 69.8 | 26.7 | 3.5 | 0.0 |
| Example 9 | | | 57.4 | | | | | 38.5 | 42.3 | 16.2 | 2.9 |
| Example 10 | | | 42.9 | | | | | 19.9 | 40.2 | 27.7 | 11.4 |
| Example 11 | | | 42.4 | | | | | 62.3 | 31.5 | 6.0 | 0.3 |
| Example 12 | | | 24.1 | | | | | 37.7 | 43.4 | 17.0 | 1.5 |
| Example 13 | | | 42.7 | 48.1 | | | | 64.6 | 29.9 | 5.4 | 0.1 |
| Example 14 | | | 57.4 | | | | | 46.3 | 42.0 | 10.7 | 1.0 |
| Example 15 | | | 53.7 | | | | | 34.6 | 42.8 | 17.1 | 5.5 |
| Example 16 | | | 53.7 | | | | | 38.4 | 39.2 | 15.5 | 6.9 |
| Comparative Example 1 | | | | | | | | 100.0 | 0.0 | 0.0 | 0.0 |
| Comparative Example 2 | | | | | | | 78.0 | 27.2 | 41.2 | 20.8 | 10.6 |
| Comparative Example 3 | | | | | 46.4 | 27.9 | | 34.9 | 43.7 | 17.8 | 3.5 |

TABLE 1-continued

| | | Evaluations | | | | | | |
|---|---|---|---|---|---|---|---|---|
| | | Component proportion of each ester compound having one or more benzoyloxy or naphthoyloxy groups (a) in ester compound mixture | | | | | | |
| | | % by mole | % by mass | | | | | |
| | | Four groups (a) | Total of components with one or more groups (a) | Total of components with one or more groups (a) | Hydrolysis resistance | Residual percentage (% by mass) | 40° C. Kinetic viscosity (mm²/s) | 100° C. Kinetic viscosity (mm²/s) | Pour point (° C.) |
| | Example 1 | 0.8 | 68.2 | 67.7 | 1 | 60.9 | 49.4 | 6.5 | −41 |
| | Example 2 | 0.4 | 66.0 | 64.8 | 1 | 76.5 | 51.5 | 7.2 | −43 |
| | Example 3 | 0.3 | 65.6 | 63.8 | 1 | 78.4 | 62.1 | 8.1 | −40 |
| | Example 4 | 5.8 | 93.7 | 93.5 | 1 | 82.7 | 207.0 | 12.1 | −24 |
| | Example 5 | 27.8 | 99.5 | 99.5 | 1 | 92.1 | 1363.2 | 22.6 | −24 |
| | Example 6 | 0.2 | 65.0 | 62.5 | 1 | 81.1 | 88.4 | 10.8 | −39 |
| | Example 7 | 0.7 | 81.6 | 80.1 | 1 | 59.5 | 98.2 | 10.3 | −31 |
| | Example 8 | 0.0 | 30.2 | 28.0 | 1 | 85.8 | 70.6 | 10.3 | −36 |
| | Example 9 | 0.0 | 61.5 | 58.1 | 1 | 83.1 | 99.6 | 12.1 | −40 |
| | Example 10 | 0.8 | 80.1 | 77.6 | 1 | 81.0 | 119.4 | 12.2 | −32 |
| | Example 11 | 0.0 | 37.7 | 35.8 | 1 | 81.9 | 59.9 | 9.0 | −44 |
| | Example 12 | 0.3 | 62.3 | 60.7 | 1 | 70.9 | 59.8 | 8.3 | −43 |
| | Example 13 | 0.0 | 35.4 | 33.6 | 1 | 88.3 | 450.5 | 25.8 | −24 |
| | Example 14 | 0.0 | 53.7 | 49.6 | 1 | 73.3 | 68.0 | 9.4 | −45 |
| | Example 15 | 0.0 | 65.4 | 62.0 | 1 | 77.9 | 164.2 | 15.7 | −30 |
| | Example 16 | 0.0 | 61.6 | 58.0 | 1 | 79.1 | 178.7 | 16.5 | −28 |
| | Comparative Example 1 | 0.0 | 0.0 | 0.0 | 2 | 55.4 | 22.3 | 4.7 | −35 |
| | Comparative Example 2 | 0.2 | 72.8 | 71.7 | 1 | 25.5 | 115.5 | 9.6 | −27 |
| | Comparative Example 3 | 0.1 | 65.1 | 65.3 | 3 | 18.2 | 72.7 | 8.0 | −29 |

In Table 1, individual symbols show the following:

PET: pentaerythritol (manufactured by Tokyo Chemical Industry Co., Ltd.),

TMP: trimethylolpropane (manufactured by Tokyo Chemical Industry Co., Ltd.),

Ph: benzoic acid (manufactured by Tokyo Chemical Industry Co., Ltd.)

α-Naph: 1-naphthoic acid (manufactured by Tokyo Chemical Industry Co., Ltd.),

β-Naph: 2-naphthoic acid (manufactured by Tokyo Chemical Industry Co., Ltd.), nC7: enantoic acid (n-heptanoic acid, manufactured by Tokyo Chemical Industry Co., Ltd.), nC8: caprylic acid (n-octanoic acid, manufactured by Tokyo Chemical Industry Co., Ltd.), nC9: pelargonic acid (n-nonanoic acid, manufactured by Tokyo Chemical Industry Co., Ltd.), iC18: isostearic acid (Prisorine 3501, manufactured by Croda Japan K.K.), Cy: cyclohexanecarboxylic acid (manufactured by Tokyo Chemical Industry Co., Ltd.), nC5: valeric acid (manufactured by Tokyo Chemical Industry Co., Ltd.), iC9: isononanoic acid (3,5,5-trimethylhexanoic acid, manufactured by Tokyo Chemical Industry Co., Ltd.), and 2EH: 2-ethylhexanoic acid (manufactured by Tokyo Chemical Industry Co., Ltd.).

The invention claimed is:

1. A method of lubricating a sliding part, comprising:
applying a lubricant base oil comprising a mixture of ester compounds to the sliding part,
wherein the mixture of ester compounds comprises compounds each represented by a general formula (1):

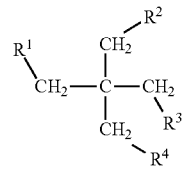

(1)

wherein $R^1$ and $R^2$ each independently represent a hydrogen atom, a methyl group, a benzoyloxy, a naphthoyloxy or a general formula (2): —O—C(=O)—$R^5$, and $R^3$ and $R^4$ each independently represent a benzoyloxy, a naphthoyloxy or the general formula (2): —O—C(=O)—$R^5$;

wherein $R^5$ represents a linear alkyl group having 5 to 21 (both inclusive) carbon atoms, a branched alkyl group having 9 to 21 (both inclusive) carbon atoms, or a cycloalkyl group having 5 to 21 (both inclusive) carbon atoms and optionally substituted with an alkyl chain, the mixture comprises compounds wherein at least two of $R^1$ to $R^4$ are the general formula (2): —O—C(=O)—$R^5$, wherein at least one $R^5$ is a linear alkyl group having 5 to 21 (both inclusive) carbon atoms and the other $R^5$ is a branched alkyl group having 9 to 21 (both inclusive) carbon atoms, and further wherein a ratio by mole of the linear alkyl group having 5 to 21 (both inclusive) carbon atoms (c) to the branched alkyl group having 9 to 21 (both inclusive) carbon atoms (d) (ratio (c)/(d)) is from 0.1 or more to 2 or less, and a proportion of a compound about which at least one of R¹ to R⁴ is the benzoyloxy or the naphthoyloxy in the mixture is from 5% or more by mole to 100% or less by mole.

2. The method according to claim 1, wherein a proportion by mass of the mixture in the lubricant base oil is from 50% or more by mass to 100% or less by mass.

3. A method of lubricating a sliding part, comprising: applying a lubricant oil composition to the sliding part, wherein the lubricant oil composition comprises the lubricant base oil according to claim 1.

4. The method according to claim 1,
wherein the compound(s) represented by the general formula (1) is yielded by condensing one or more alcohols and one or more carboxylic acids, and each represented by the general formula (1),
wherein the alcohol(s) comprise(s) a polyhydric alcohol represented by a general formula (3):

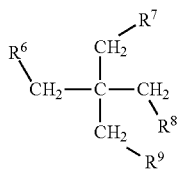

(3)

wherein R⁶ to R⁹ each independently represent a hydrogen atom, a methyl group or a hydroxyl group, and further at least two of R⁶ to R⁹ each represent the hydroxyl group, the carboxylic acid(s) comprise(s) one or more aromatic carboxylic acids and one or more aliphatic carboxylic acids, the aromatic carboxylic acid(s) comprise(s) benzoic acid and/or naphthoic acid, and the aliphatic carboxylic acid(s) comprise(s) at least one monocarboxylic acid selected from linear alkyl aliphatic acids each having 6 to 22 (both inclusive) carbon atoms, branched alkyl aliphatic acids each having 10 to 22 (both inclusive) carbon atoms, and cycloalkanecarboxylic acids each having 6 to 22 (both inclusive) carbon atoms and each optionally substituted with an alkyl chain.

5. The method according to claim 4, wherein the aromatic carboxylic acid(s) comprise(s) benzoic acid, and the linear alkyl aliphatic acids each having 6 to 22 (both inclusive) carbon atoms comprise n-heptanoic acid.

6. The method according to claim 4, wherein the aromatic carboxylic acid(s) comprise(s) benzoic acid, and the branched alkyl aliphatic acids each having 10 to 22 (both inclusive) carbon atoms comprise isostearic acid.

7. The method according to claim 4, wherein the aromatic carboxylic acid(s) comprise(s) benzoic acid, the linear alkyl aliphatic acids each having 6 to 22 (both inclusive) carbon atoms comprise n-heptanoic acid, and the branched alkyl aliphatic acids each having 10 to 22 (both inclusive) carbon atoms comprise isostearic acid.

8. The method according to claim 4, wherein for 100 equivalents of the polyhydric alcohol,
an amount of carboxyl groups of the aromatic carboxylic acid(s) is from 10 to 90 equivalents both inclusive,
an amount of carboxyl groups of the aliphatic carboxylic acid(s) is from 60 to 140 equivalents both inclusive, and further
a total amount of the carboxyl groups of the aromatic carboxylic acid(s) and the aliphatic carboxylic acid(s) is from 100 to 150 equivalents both inclusive.

9. The method according to claim 1,
wherein a ratio by mole of the general formula (2): —O—C(=O)—R⁵ (a) to the whole of the benzoyloxy and naphthoyloxy (ratio (a)/(b)) is from 0.1 or more to 10 or less.

10. The method according to claim 1,
wherein a ratio by mole of the linear alkyl group having 5 to 21 (both inclusive) carbon atoms (c) to the whole of the benzoyloxy and naphthoyloxy (ratio (c)/(b)) is from 0.3 or more to 2 or less.

11. The method according to claim 1,
wherein the proportion of the compound about which at least one of R¹ to R⁴ is a benzoyloxy or naphthoyloxy group in the mixture is from 35% or more by mole to 99% or less by mole.

12. The method according to claim 1,
wherein a proportion by mass of the compound about which at least one of R¹ to R⁴ is a benzoyloxy or naphthoyloxy in the mixture is from 30% or more by mass to 95% or less by mass.

13. The method according to claim 1,
wherein the 40° C. kinetic viscosity of a condensed ester comprising the compound(s) represented by the general formula (1) is from 30 mm²/s or more to 1500 mm²/s or less, and the 100° C. kinetic viscosity of the condensed ester is from 5 mm²/s or more to 20 mm²/s or less.

14. The method according to claim 1,
wherein the pour point of a condensed ester comprising the compound(s) represented by the general formula (1) measured by a measuring method according to JIS K2269 is −20° C. or lower.

15. The method according to claim 4,
wherein the polyhydric alcohol is at least one species selected from the group consisting of pentaerythritol, trimethylolpropane, and neopentyl glycol.

16. The method according to claim 4,
wherein a proportion of the aromatic carboxylic acid(s) in the carboxylic acid(s) is from 10% or more by mole to 90% or less by mole.

17. The method according to claim 4,
wherein a proportion of the linear alkyl aliphatic acid(s) having 6 to 22 (both inclusive) carbon atoms in the carboxylic acid(s) is from 20% or more by mole to 70% or less by mole.

18. The method according to claim 4,
wherein a proportion of the branched alkyl aliphatic acids each having 10 to 22 (both inclusive) carbon atoms in the carboxylic acid(s) is from 10% or more by mole to 50% or less by mole.

19. The method according to claim 4,
wherein a proportion of the cycloalkanecarboxylic acids each having 6 to 22 (both inclusive) carbon atoms and each optionally substituted with an alkyl chain in the carboxylic acid(s) is from 10% or more by mole to 70% or less by mole.

20. The method according to claim 3,
wherein a proportion by mass of the lubricant base oil in the lubricant oil composition is from 90% or more by mass.

* * * * *